(12) United States Patent
Wen

(10) Patent No.: US 6,776,824 B2
(45) Date of Patent: Aug. 17, 2004

(54) ANTIVIRAL AND ANTIBACTERIAL FILTRATION MODULE FOR A VACUUM CLEANER OR OTHER APPLIANCE

(76) Inventor: Sheree H. Wen, 796 Longhill Rd. West, Briarcliff Manor, NY (US) 10510

( * ) Notice: Subject to any disclaimer, the term of this patent is extended or adjusted under 35 U.S.C. 154(b) by 0 days.

(21) Appl. No.: 10/044,381

(22) Filed: Jan. 11, 2002

(65) Prior Publication Data

US 2003/0131439 A1 Jul. 17, 2003

(51) Int. Cl.$^7$ ............................................. B01D 50/00
(52) U.S. Cl. ............................. 96/223; 96/224; 96/226; 55/485; 55/486; 55/DIG. 3
(58) Field of Search .......................... 96/223, 224, 226, 96/227; 55/485, 486, DIG. 3; 15/344, 353

(56) References Cited

U.S. PATENT DOCUMENTS

| | | | |
|---|---|---|---|
| 1,891,256 A | * 12/1932 | Bilde ........................... | 96/222 |
| 3,230,033 A | 1/1966 | Hamilton et al. | |
| 3,478,758 A | 11/1969 | Davies | |
| 3,817,703 A | 6/1974 | Atwood | |
| 3,915,180 A | 10/1975 | Jacobs | |
| 3,926,556 A | 12/1975 | Boucher | |
| 4,207,286 A | 6/1980 | Gut Boucher | |
| 4,468,372 A | * 8/1984 | Seifert et al. .................. | 96/52 |
| 4,513,470 A | 4/1985 | Toya | |
| 4,536,914 A | 8/1985 | Levine | |
| 4,542,557 A | 9/1985 | Levine | |
| 4,577,365 A | 3/1986 | Yuen | |
| 4,591,485 A | 5/1986 | Olsen et al. | |
| 4,610,048 A | 9/1986 | Ishihara et al. | |
| 4,836,684 A | 6/1989 | Javorik et al. | |
| 4,924,548 A | 5/1990 | Touya et al. | |
| 5,120,499 A | 6/1992 | Baron | |
| 5,244,629 A | 9/1993 | Caputo et al. | |
| 5,288,298 A | * 2/1994 | Aston ........................... | 96/135 |
| 5,320,805 A | 6/1994 | Kramer et al. | |
| 5,364,645 A | 11/1994 | Lagunas-Solar | |
| 5,492,882 A | 2/1996 | Doughty et al. | |
| 5,589,396 A | 12/1996 | Frye et al. | |
| 5,593,476 A | 1/1997 | Coppom | |
| 5,647,890 A | 7/1997 | Yamamoto | |
| 5,651,811 A | 7/1997 | Frey et al. | |
| 5,656,063 A | 8/1997 | Hsu | |
| 5,725,623 A | 3/1998 | Bowerman et al. | |
| 5,779,769 A | 7/1998 | Jiang | |
| 5,927,304 A | 7/1999 | Wen | |
| 5,944,873 A | 8/1999 | Jager et al. | |
| 6,029,712 A | 2/2000 | Dougherty | |
| 6,056,808 A | 5/2000 | Krause | |
| 6,063,170 A | * 5/2000 | Deibert ......................... | 96/224 |
| 6,094,775 A | 8/2000 | Behmer | |
| 6,171,375 B1 | 1/2001 | Howie | |
| 6,190,437 B1 | * 2/2001 | Forsyth ......................... | 95/90 |
| 6,203,600 B1 | 3/2001 | Loreth | |
| 6,295,692 B1 | 10/2001 | Shideler | |
| 6,296,692 B1 | 10/2001 | Gutmann | |
| 6,333,004 B1 | * 12/2001 | Sheldon ........................ | 422/4 |
| 6,434,785 B1 | * 8/2002 | Vandenbelt et al. ........... | 15/344 |
| 6,468,433 B1 | * 10/2002 | Tribelski ...................... | 210/748 |
| 2001/0043887 A1 | 11/2001 | Morneault | |

FOREIGN PATENT DOCUMENTS

| | | |
|---|---|---|
| DE | 3739979 A1 | 6/1989 |
| FR | 2599255 | 12/1987 |
| GB | 947699 | 9/1961 |
| GB | 2162424 | 2/1986 |
| JP | 62-282686 | 12/1987 |
| JP | 2-43984 | 2/1990 |

\* cited by examiner

*Primary Examiner*—Robert A. Hopkins
(74) *Attorney, Agent, or Firm*—Robert D. Katz; Cooper & Dunham LLP

(57) ABSTRACT

The invention provides a portable or hand-held vacuum cleaner that includes a filtration system or filtration module that can pick up particles and contaminants. It has a first passive stage (such as a HEPA filter) to collect dust particles, and contaminants over a predetermined size. The invention also includes an active stage filter(such as an ozone generator) which may include one or more chemical (or biological) agents effective to kill bacteria, viruses, and the like.

21 Claims, 5 Drawing Sheets

ANTIVIRAL AND ANTIBACTERIAL FILTRATION MODULE FOR A VACUUM CLEANER OR OTHER APPLIANCE

FIELD OF THE INVENTION

This invention relates to a device for removing or destroying ambient bacteria, viruses, and the like. More particularly, this invention relates to a filtration system for use in portable, hand-held, upright, or canister vacuums, and to vacuum cleaners that incorporate or include such modules therein.

BACKGROUND OF THE INVENTION

Airborne bacteria and viruses cause infection and disease through nasal inhalation, among other means, and pose a danger if spread accidentally or intentionally in the atmosphere. Likewise, various gasses, for example, such as sarin and cyanide pose an extreme or lethal health threat, if released into a populated civilian or military area. Further, various chemical and biological agents which are applied to or settle on surfaces such as flooring, rugs or carpets, and furniture can be absorbed through the skin or mucous membranes of an individual who comes into contact with such agents. Prior attempts to provide a system which can collect and destroy biological agents, including bacteria and viruses (not limited to those small enough to pass through a HEPA filter), as well as absorb or neutralize chemical agents, including poisonous gasses, liquids or solids, which can be inhaled or absorbed by an individual who comes into contact with one or more such agents, appear to provide an incomplete solution to the hazards posed by exposure to such agents.

U.S. Pat. No. 4,536,914 (Levine) discusses a wet-dry portable vacuum cleaner suitable to clean up both liquid and solid spills. According to the patentee, the cleaner has a blower, a motor, a canister having a nozzle, and a storage chamber beneath the nozzle. The intake port has a liquid deflecting hood extending from an upper portion thereof into the chamber for deflecting any liquid exiting from a posterior port of the nozzle into the chamber, as discussed in the foregoing patent, and its companion, U.S. Pat. No. 4,542,557 (Levine).

U.S. Pat. No. 4,610,048 (Ishihara) provides a hand-held vacuum cleaner having a first section comprising an extendable telescoping opening connected to a second section that comprises a motor, fan handle, and filter. The two sections are joined together by a locking mechanism that provides a snug fit to prevent leaks between the two units. The telescoping opening permits access to areas that might not otherwise be accessible to a hand-held vacuum cleaner.

U.S. Pat. No. 4,577,365 (Yuen) discloses a rechargeable vacuum cleaner that includes a front portion with an intake nozzle, a body portion and a handle portion, with the body portion mounting a motor fan suction unit and a filter, and having outlet apertures therein for air from the motor fan suction unit. The filter includes a disk of flexible filter material sandwiched between two annular members, one of which defines a grid framework over which the disk of flexible filter material is stretched when one of the members is telescopically received within the other of the members with the filter material located therebetween.

U.S. Pat. No. 4,924,548 (Touya) discusses a portable vacuum cleaner for use in both dry and wet operations. It has a main body case housing, a fan motor, intake and discharge openings, and a dust case having an intake portion that is removable from the main body case at the intake opening. It also has a filter housing with a filter covering the intake opening.

Each of the foregoing patents, incorporated herein in its entirety, does not appear to provide a vacuum cleaner or similar appliance that can absorb or destroy chemical or biological contaminants on the surface in a given area.

SUMMARY OF THE INVENTION

In a first embodiment, the invention provides a portable or hand-held vacuum cleaner that includes a filtration system or filtration module that can pick up particles and contaminants. It has a first passive stage to collect dust particles, and contaminants over a predetermined size. For example, the passive stage may include a HEPA filter to collect particles above about $0.3\mu$, with or without activated charcoal to absorb odors or noxious gasses. The vacuum cleaner also includes an active stage filter which may include one or more chemical (or biological) agents effective to kill bacteria, viruses, spores, fungi and the like. Preferably, it includes a UV or other radiation source capable of creating ozone from atmospheric oxygen, such that the ozone destroys bacteria viruses and other biological contaminants.

In a second embodiment, the invention provides an upright, canister or backpack (see, e.g., U.S. Pat. No. 6,295,692, incorporated herein by reference) vacuum cleaner which may be used in a home, office, hotel, factory, or other public space. This vacuum cleaner, like the previous embodiment, includes a two stage filtration system or filtration module that can collect debris, particles and most contaminants, as well as an active stage to destroy bacteria or other biological contaminants too fine to trap in the first stage filter.

In yet another embodiment, the invention provides a filtration module, cartridge or insert for a portable, hand-held, upright or canister vacuum cleaner or other appliance, which includes a two stage, passive/active filtration system as mentioned above, and discussed in more detail below.

In still another embodiment, the invention provides a filtration and sanitation module that can be incorporated into another appliance, such as a refrigerator, conventional or microwave oven, dishwasher, or the like, to help kill contaminants on articles placed therein.

BRIEF DESCRIPTION OF THE DRAWINGS

Further objects, features, and advantages of the invention, will become apparent upon review of the following detailed description of the preferred embodiments, taken together with the attached drawings in which.

DETAILED DESCRIPTION OF THE PREFERRED EMBODIMENTS

Figure 1:
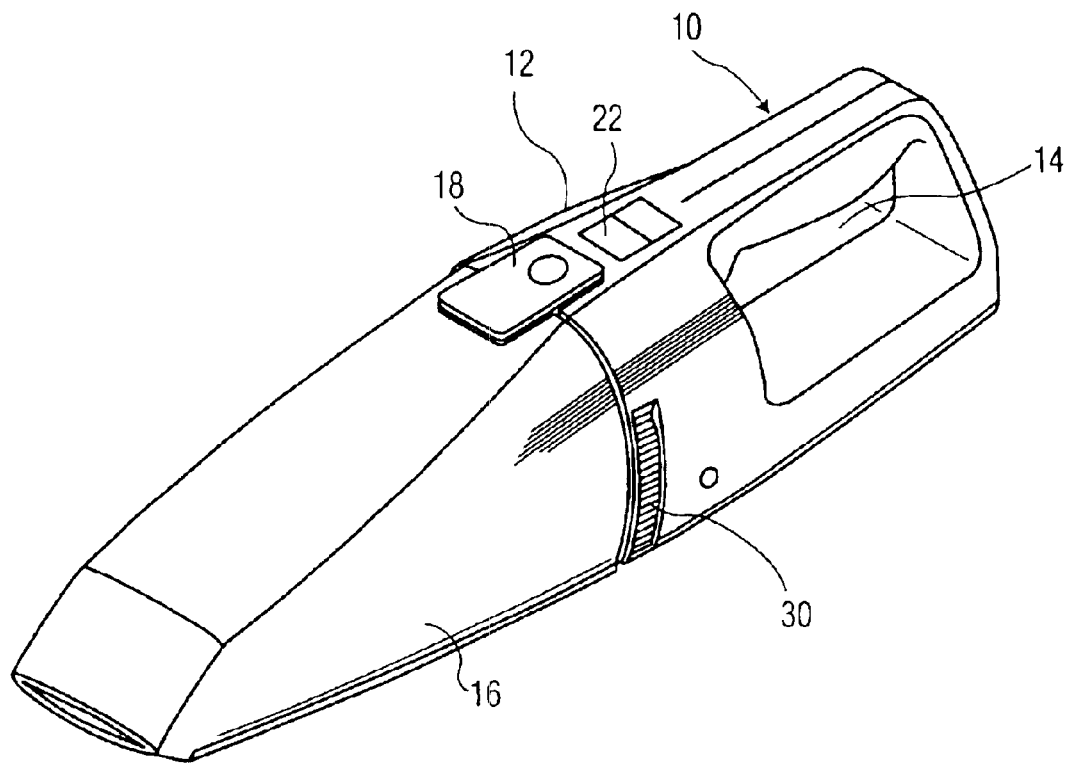
FIG. 1 is a perspective view of a hand-held vacuum in accordance with the present invention.
Figure 2:
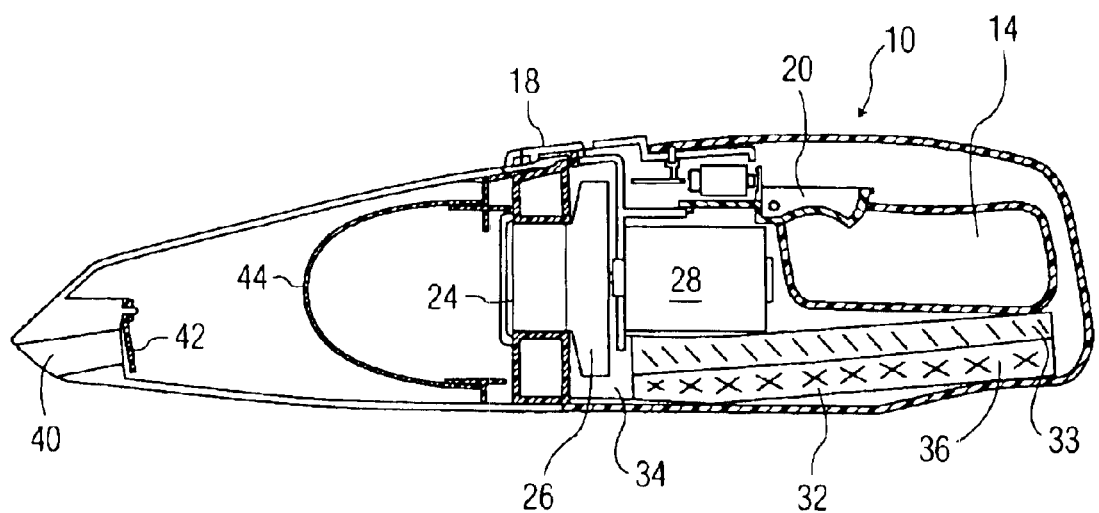
FIG. 2 is a longitudinal sectional view showing the interior construction of the hand-held vacuum of FIG. 1.

FIGS. 1 and 2 illustrate a hand-held or portable vacuum cleaner in accordance with the present invention, generally designated by the reference numeral 10. The hand-held vacuum 10 includes a main body housing 12 including a handle 14 connected to an intake housing 16 by one or more clips 18. A trigger switch 20, as shown in FIG. 2, may actuate the vacuum 10, as may a toggle or pressure switch 22, as shown in FIG. 1. The main body 12 encases the motor 24, the fan 26, and the power source 28, which may be, for example, a rechargeable NiCd or LiH battery. A conventional vacuum cleaner recharging transformer (not shown) recharges the power source 26 in the vacuum 10. The vacuum cleaner 10 may include exhaust ports 30 on the housing 16 outside the fan 26. The front portion of the vacuum cleaner 10 includes an inlet 40, a door 42 retain dust and a conventional filter 44 to trap dust and debris.

An important feature of the present invention lies in the two-stage filtration system 32, shown in FIG. 1, which can filter out or adsorb ambient biological and chemical contaminants. The filtration system 32 includes an opening 34 from the fan 26 through which intake air passes. The filtration system 32 includes a passive, physical filter, capable of removing particles above a certain size from the air (usually about $0.3\mu$). It also includes an active filtration stage 36 to remove or destroy biological contaminants (whether naturally occurring or manmade) such as bacteria, spores, and viruses (or other contaminants), which are too small to be trapped by a HEPA filter. The filtration system may optionally include an adsorbent filter of activated charcoal or the like, to remove odors and hazardous chemicals, including toxic and odorous gasses before permitting it to escape through the exhaust ports 30 (see FIG. 1). The construction of the filtration system may be understood by reviewing the discussion below, and my co-pending patent application, U.S. patent application Ser. No. 10/023, 961, filed Dec. 18, 2001, the contents of which are incorporated herein by reference.

More particularly, the first stage accomplishes filtration of most chemical and biological contaminants using activated charcoal or other similar filtration materials with extremely large surface areas per unit volume of material. The filtration stage that physically adsorbs a contaminant, whether in solid, liquid, or gaseous form, or as vapors or particles mixed or suspended in air, can use many adsorbent materials known to those skilled in the art, including, without limitation: activated carbon, alumina, silica gel, bentonite, diatomaceous earth, ion exchange resins, powdered zeolites (both natural and synthetic), molecular sieves, and catalytic particles. The passive or physical filtration portion can also (or alternatively) include a HEPA filter, which can filter out particles down to about 0.5 to 0.3$\mu$ in size.

The second stage of the filter, the active stage, includes one or more agents which can destroy, inactivate, or render harmless biological materials, including bacteria, viruses, and the like, which could cause widespread infection, if inhaled, which includes a UV light source capable of forming ozone from ambient oxygen.. Using the two-stage filter, the active stage will kill bacteria, spores and viruses that may be too small to be blocked by passive filter stage, for example, Bacillus Anthracis, *Agrobacterium tumefaciens, Bacillus magaterium* (vegetative), *Bacillus subtillis* (vegetative), *Bacillus paratyphusus, Bacillus tetani, Clostridium tetani, Corynebacterium diptheriae, Eberthella typosa, Escherichia coli, Leglonella bozimanil, dumoffil, gormanii, Legionella, longbeachae, pneumophila, Legionella nicadel, Legionella interrogans* (infectious jaundice), *Mycobacterium tuberculosis, Neisseria catarrhaiis, Phtomonas tumeficiens, Proteus vulgaris, Psuedomonas aeruginosa* (laboratory & environmental), *Psuedomonas fluorescens,* Rhodospirilum Rubrum, Salmonella Enteritidis, *Salmonella paratyphi* (Enteric Fever), *Salmonella tyhimurium, Salmonella typosa* (Typhoid fever), *Sarcina lutea, Serratia marcescens, Shigella dysenteriae, flexneri* (Dysentery), *Shigella paradysenteriae, Shirililum rburum, Staphylococcus, aureus, epidermidis, faecilis, Staphylococcus hemolyticus, lactis, viridans, Streptococcus faecalis, hemolyticus, lactis, Vibrio Cholerae,* and spores, including anthrax spores, *Aspergillus flavus, Aspergillus flaucus, Aspergillus glaucus, Aspergillus niger, Bacillus magaterium, Bacillus subtillis, Mucor ramosissimus,* Oospora, *Penicillum digitatum, Penicillum expensum, Penicillum roqueforti, Rhizopus nigticans,* and Saccharomyces. The active stage can also kill algae, including, *Chlorella vulgaris,* protozoa, such as Nemotode eggs, Paramecium, and viruses, including small pox, Bacteriophage (*E. Coli*), Hepatitis (all forms), influenza, poliovirus, rotavirus, tobacco mosaic virus, ebola virus, and other infectious viruses. Similarly, the active ingredient or ingredient should be able to kill yeast and fungi, including Baker's yeast, Brewer's yeast, Common yeast cake, *Saccharomyces ellipsoideus,* and cysts, such as, *Glaria llamblia* and Chryposporidium.

The active ingredient can be one or more of the following substances, known to destroy or render harmless any of the foregoing bacterial, or other biological contaminants, including sterilizing ingredients such as chlorohexidine, ethanol, lysostaphin, benzoic add analog, lysine enzyme and metal salt, bacitracin, methicillin, cephalosporin, polymyxin, cefaclor, Cefadroxil, cefamandole nafate, cefazolin, ceflxime, cefinetazole, cefonioid, cefoperazone, ceforanide, cefotanme, cefotaxime, cefotetan, cefoxitin, cefpodoxime proxetil, ceftaxidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and chelating agents in an amount effective to enhance the effect of the lysine enzyme. In addition to or instead of a chemical or biochemical agent, the active stage may include one or more metallic agents, in the form of a mesh or other configuration, which can destroy ambient bacterial or viral agents. The metals may include silver, zinc, titanium, copper, or iron oxide. The active barrier may also include a chamber with microelectrical plates or magnetic coils, which generate electromagnetic energy in a form and at a strength sufficient to kill bacteriological contaminants.

The active portion of the filter should preferably also include a UV light or an apparatus for generating a magnetic or electric field capable of emitting radiation powerful enough to destroy bacteria and viruses. It should also include a UV or electric discharge to create ozone form ambient oxygen, which ozone destroys airborne bacterial and viral contaminants, and oxidizes chemical contaminants, including cyanide. The battery 28 that powers the blower 26 also runs the UV light or other electromagnetic radiation generator. In a preferred embodiment, the active portion of the filter includes zinc mesh as an antibacterial and antiviral agent. The filter media, both active and passive, may be removed and replaced without exposing the user to any hazard. Where one or more active ingredients are sensitive to exposure to air, the replacement filter cartridge or modules can be packed in foil or plastic, and opened just prior to use. Ukewise, where the active ingredient needs moistening to activate it, the substance can be packaged with a burstable bubble package that contains water or other suitable solvent. Alternatively, it can be activated, if necessary, using available water or liquid.

One presently preferred embodiment of the filtration module includes a UV lamp that destroys most bacteria and viruses directly, and also creates ozone from oxygen in the atmosphere, which in turn kills any remaining bacteria, viruses, spores or other contaminants, and oxidizes any chemical contaminants, including cyanide. To avoid release of ozone into the environment, the exhaust gas can be filtered through the activated carbon or other adsorbent medium in the passive stage, passed through water (to form hydrogen peroxide), or passed through a metallic mesh or grid, such as zinc (to form zinc oxide). Importantly, the by-products of ozone degradation have biological contaminant destroying ability, as well. Alternatively, the ozone laden fluid stream can be passed through a vegetable (or mineral) oil such as soybean or olive oil to filter out ozone.

Figure 3:
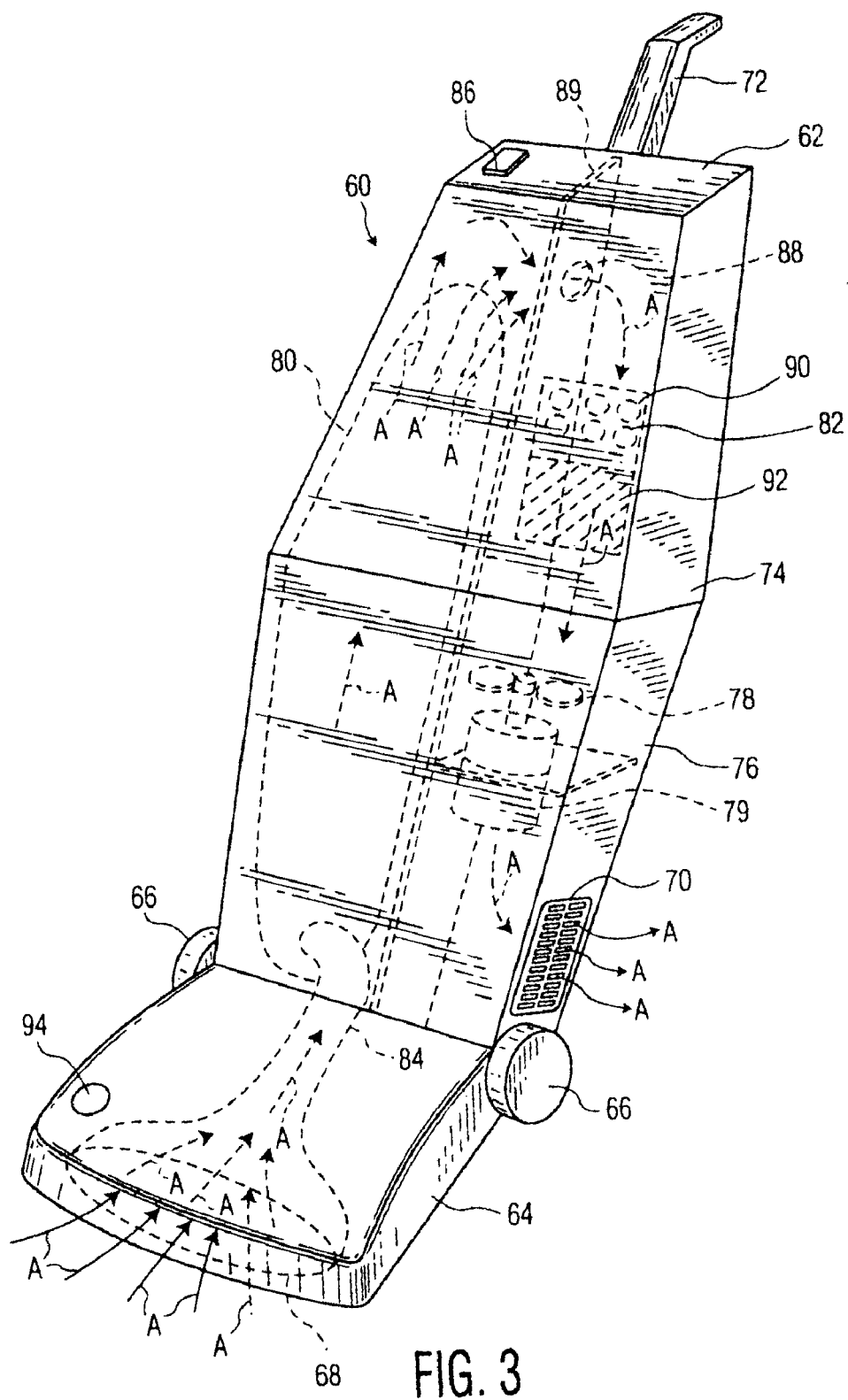
FIG. 3 is a perspective view of an upright vacuum incorporating the present invention.

In another embodiment shown in FIG. 3, an upright vacuum cleaner 60 includes the improved filtration system of the present invention. Preferably, the upright vacuum cleaner 60 has an internal dust collection chamber 80. The present invention may also be incorporated in an upright vacuum cleaner with an external soft-sided dust collection bag, as exemplified by U.S. Pat. No. 5,725,623, incorporated herein by reference, by inserting a filtration cartridge or canister in the airflow path, or by incorporating the two stage filtration system into the layers of the filter bag. In the exemplary preferred embodiment shown in FIG. 3, the vacuum cleaner 60 includes a housing 62, a floor sweeper 64, a pair of wheels 66, an intake opening 68, an exhaust port 70, and a handle 72. The housing 62 divides into upper 74 and lower 76 sections, which cover the internal mechanism of the vacuum (shown in phantom), including fan or blower 78, motor 79, collection bag 80, and the improved supplemental filtration system 82 of the present invention. By depressing switch 86, contaminated or partide laden air A enters the upright vacuum 60 through inlet 68 and is carried by conduit 84 into collection bag 80, which traps most dust and other particles in a bag made of conventional materials including paper, polymers, meshes, and woven fabrics known to those skilled in the art, as discussed for example in U.S. Pat. No. 5,651,811, and patents cited therein, which are incorporated herein by reference.

Air A continues through opening 88 in baffle into filtration cartridge or canister 82. Preferably, the filtration cartridge or canister 82 includes a passive stage 90 to filter out remaining particles and biological contaminants over a predetermined size (such as 0.3µ particles); e.g., particles trapped by a HEPA filter. Air A continues through the active stage 92, which includes one or more agents effective to destroy any bacteria, spores, viruses, or other untrapped biological contaminants, as well as UV or other radiation source capable of sterilizing a given volume of air passing through, or creating ozone to add to the antiseptic effect. Filter unit 82 may be replaced when filled or inactive, and may include a sensor (not shown) to indicate when replacement would be desirable. After passing through the passive stage 90, the air A contains no contaminants, and may return to the atmosphere through exhaust port 70, filtering out ozone through water, a metallic mesh, or by use of a catalytic agent to render the ozone inert. The upright vacuum 60 may include additional intake tools such as hoses, wands and the like (not shown) attachable through retractable port 94.

Figure 4:
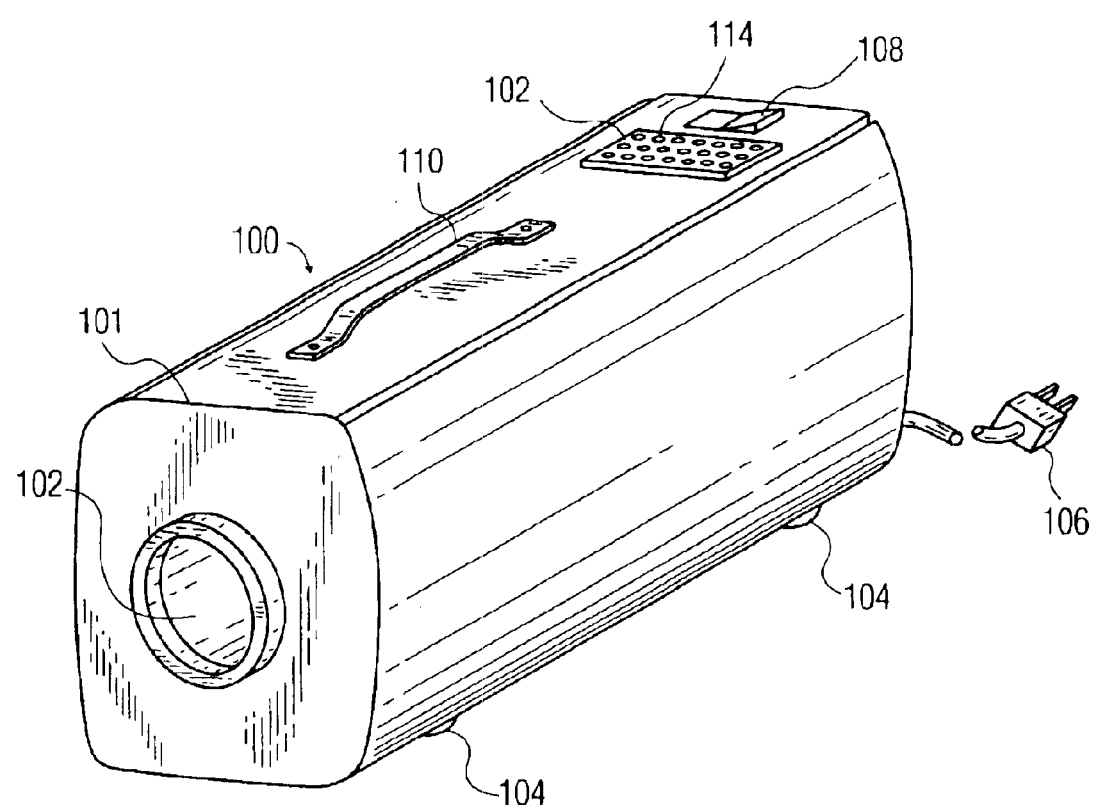
FIG. 4 is a perspective view of a canister vacuum incorporating the present invention.
Figure 5:
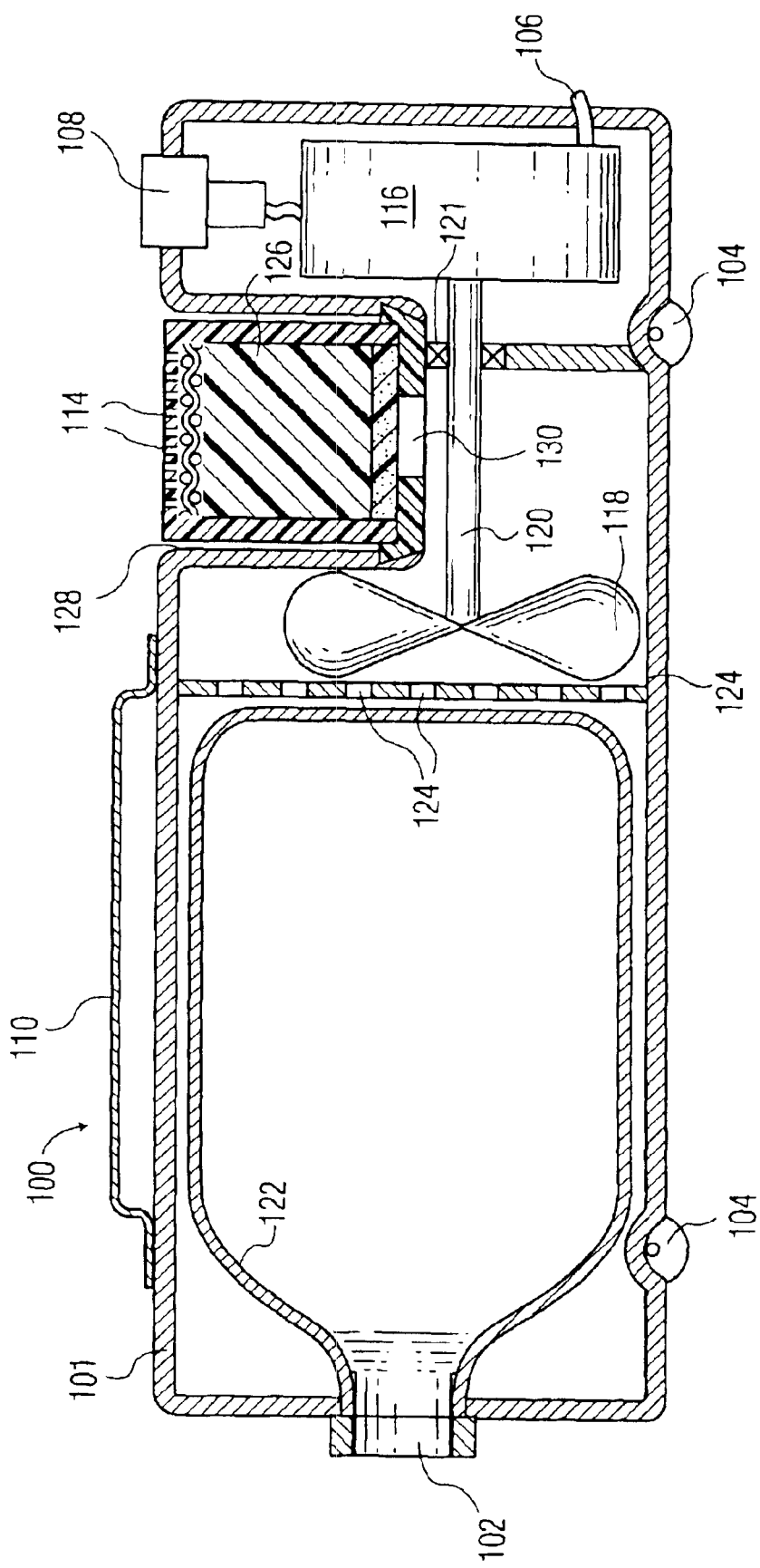
FIG. 5 is a longitudinal sectional view showing the filter system of the present invention incorporated into the canister vacuum of FIG. 4.

FIGS. 4 and 5 illustrate a canister vacuum deaner 100 including the present invention. The canister 100 has a housing 101 with an inlet 102, wheels 104, power source 106 (which may be an electric plug), switch 108, handle 110, and exhaust port 112, having a plurality of openings 114 through which exhaust air can flow.

Referring to FIG. 5, electric motor 116 turns blower fan 118 via shaft 120 captured by bearing 121. Dust bag 122 traps most airborne particles, and its exhaust passes through openings 124 past fan 118 and an opening 130 to permit further filtration in filter cartridge 126 mounted in receptacle 128 formed in the housing 100. Filter cartridge 126 includes, as with the other embodiments of the invention, at least two stages: a passive stage (such as a HEPA filter), and optionally an odor and chemical hazard absorbing agent (such as activated charcoal); and an active stage which includes at least one agent, as set forth above, in an amount effective to destroy ambient biological contaminants that pass through both the conventional vacuum cleaner bag 122 and the passive stage of the advanced filtration cartridge 126. The active stage includes the ingredient capable of destroying biological contaminants, as well as a radiation source (such as UV or IR), that can destroy biological contaminants, preferably, directly and indirectly, through the ozone generating mechanism discussed above.

Figure 6:
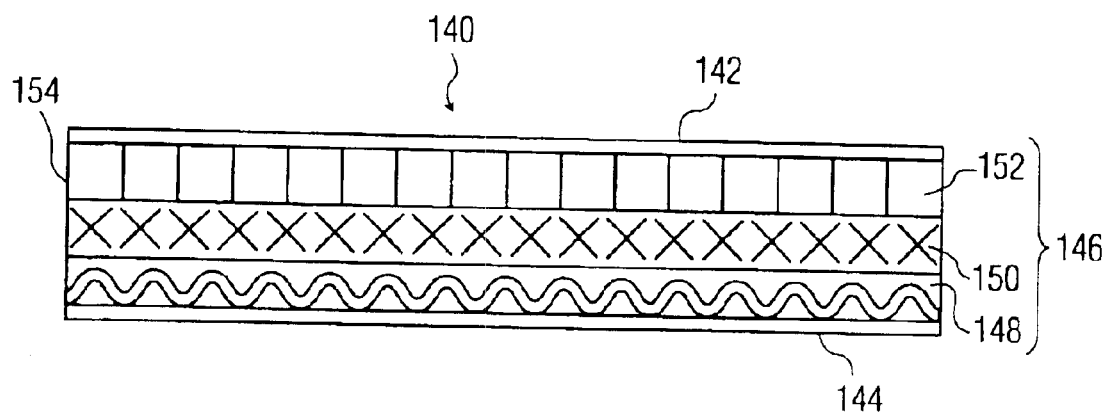
FIG. 6 is a sectional view of a filter module for use in a vacuum cleaner or other appliance.

Another embodiment of the present invention, illustrated in FIG. 6, provides a dual stage filter 140 for removal or destruction of airborne contaminants. As with other embodiments, the filter 140 includes both a passive and active filtration stage. The filter 140 is shaped to fit in a desired chamber, so that the filter 140 attaches or may be attached securely. The filter 140 includes highly porous intake 142 and exhaust 144 layers (preferably made of fiberglass or other polymer fibers) which sandwich a first stage 146 containing passive filtration media 148, such as activated charcoal or one of the other materials discussed above in connection with the other embodiments. The passive stage also includes a HEPA filter 150 to remove particles, including bacteria and other biological agents, which have a particle size over about 0.3µ.

The second stage 152 or active portion of the filtration element 140 includes one or more active ingredients 154, as discussed above, to kill bacteria or viral contaminants which pass through the passive stage 146 of the filter cartridge 140. The active portion 152 can also include a miniaturized UV light capable of creating ozone or an apparatus for generating a magnetic or electric field capable of destroying bacteria and viruses 56. A battery (not shown) provides power, if necessary, to run the UV light and generate the desired fields. In a preferred embodiment, the active portion 152 includes zinc mesh as an antibacterial and antiviral agent. The filter media, both active and passive, may be removed and replaced when the active media has expired, or the passive stage becomes clogged with particulates.

Figure 7:
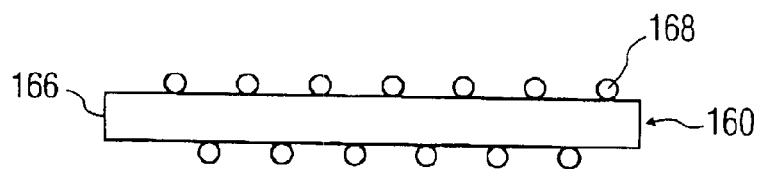
FIG. 7 is a further embodiment of the filter of FIG. 6.

In yet another embodiment, illustrated in FIG. 7 (a variation on the active/passive filter embodiment of FIG. 6), the insert 160 includes an effectively single layer, although it has both active and passive components. The insert may comprise, for example, a breathable or porous woven cloth or paper filter 66 impregnated with polyvinylpyrolidone-iodine, a well-known antiseptic 68. The active ingredient may be moistened to release the antiseptic. It may optionally include a UV light or other radiation source to help kill biological contaminants.

As can be appreciated by a person of ordinary skill, the two stage filtration unit can come in many sizes and shapes, and can be used in other appliances to help ensure sanitary conditions. For example, an elongated filtration cartridge including, for example, a passive filter stage, an active filter stage (which may include a chemical agent, a metallic agent, and a radiation source), may be fitted in a kitchen appliance. That is, a refrigerator can have an insert installed in a desired compartment, for meat and produce or the like, and the insert can include or be connected to a power source to operate a fan and a radiation source. Likewise, a dishwasher can include an insert which removes biological and chemical contaminants to enable it to wash and sanitize vegetables, fruit and other produce.

While the present application shows and describes particular embodiments of the present invention, those of ordinary skill in the art will recognize that many changes and modifications may be made therein without departing from the spirit or scope of the invention. Accordingly, it is intended to cover all alternatives, modifications, and equivalents as may reasonably be included based upon a fair and accurate interpretation and application thereof.

What is claimed is:

1. A hand-held vacuum cleaner comprising:
   a vacuum cleaner body having a handle, and housing an electric powered blower powered by a battery with a switch disposed between the battery and the blower;
   an intake portion releasably connected to the vacuum cleaner body such that the intake stage forms an airtight seal with the vacuum body;
   the vacuum cleaner having an intake opening, an exhaust portion, and
   a filtration system disposed therebetween to filter contaminated air drawn through the intake opening, the filtration system including:
   a first passive stage to filter out airborne particles above a predetermined size, an active stage including an energy source and at least one agent effective to kill ambient biological contaminants, and
   a second passive stage for removing odors and hazardous chemical agents, wherein the first passive stage is sandwiched between the active stage and the second passive stage to form an integral filter.

2. A hand-held vacuum cleaner in accordance with claim 1 wherein the energy source is a UV light source, which emits UV light at a frequency and intensity effective to kill biological contaminants contained in the contaminated air, and to form ozone to oxidize chemical contaminants contained in the air.

3. A hand-held vacuum cleaner in accordance with claim 1, wherein the agent in the active stage is clorohexidine, ethanol, lysostaphin, benzoic acid analog, lysine enzyme and metal salt, bacitracin, methicillin, cephalosporin, polymyxin, cefaclor, Cefadroxil, cefamandole nafate, cefazolin, cefime, cefinetazole, cefonioid, cefoperazone, ceforanide, cefotanme, cefotaxime, cefotetan, cefoxitin, cefpodoxime proxetil, ceftaxidime, ceftizomxime, ceftrizxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihdratecephaloghin, moxalactam, or loracarbef mafate.

4. A hand-held vacuum cleaner in accordance with claim 1, wherein the agent in the active stage is lysine enzyme, and additionally comprises a chelating agent in an amount effective to enhance the effect of the lysine enzyme.

5. A hand-held vacuum cleaner in accordance with claim 1, wherein the active stage additionally comprises one or more metallic agents effective to kill ambient biological contaminants.

6. A hand-held vacuum cleaner in accordance with claim 5 wherein the metallic agent is silver, zinc, titanium, or copper mesh.

7. A hand-held vacuum cleaner in accordance with claim 1, wherein the active stage additionally comprises an IR light source, an electric or magnetic field generator.

8. A hand-held vacuum cleaner in accordance with claim 2, wherein the active stage additionally comprises an electric or magnetic field generator to separate airborne particles from contaminated air.

9. A hand-held vacuum cleaner in accordance with claim 2, wherein the electric or magnetic field generator includes microfilaments, micro electrical plates or magnetic coils.

10. A hand-held vacuum cleaner in accordance with claim 2, wherein the active ingredient is in the form of a particulate, a tablet, a tape, a mesh, a solid containing the active ingredient, or a fabric containing the active ingredient.

11. A filtration unit comprising:
    a first passive stage for filtering out particles above a predetermined size,
    an active stage containing an ultraviolet source and at least one agent to kill ambient bacteria and viruses, and
    a second passive stage including an adsorbent agent for removing odors and hazardous chemical agents, wherein the first passive stage is sandwiched between the active stage and the second passive stage to form an integral filter;
    an intake port permitting contaminated air to enter into the filtration unit; and
    an exhalation port through which decontaminated air may be expelled.

12. A filtration unit in accordance with claim 11, wherein the second passive stage includes an activated charcoal agent.

13. A filtration unit in accordance with claim 11, wherein the ultraviolet light source forms ozone in order to oxidize chemical contaminants and to kill biological contaminants.

14. A filtration unit in accordance with claim 11, wherein the agent in the active stage is chlorhexidine, ethanol, lysostaphin, benzoic acid analog thereof, lysine enzyme, bacitracin, methiclillin, cephalosporin, polymyxin, cefaclor, Cefadroxil, cefamandole nafate, cefazolin, cefixime, cefinetazole, cefonioid, cefoperazone, ceforanide, cefotanme, cefotaxime, cefotetan, cefoxitin, cefpodoxime proxetil, ceftaxidime, ceftizoxime, ceftriaxone, cefriaxone moxalactam, cefuroxime, cephalexin, cephalosporin C, cephalosporin C sodium salt, cephalothin, cphalothin sodium salt, cephapirin, cepharadine, cefuroximeaxetil, dihydratecephalothin, moxalactam, or loracarbef mafate.

15. A filtration unit in accordance with claim 13, wherein the agent in the active stage is lysine enzyme, and additionally comprises a chelating agent in an amount effective to enhance the effect of the lysine enzyme.

16. A filtration unit in accordance with claim 14, wherein the active stage additionally comprises one or more metallic agents effective to kill bacteria and viruses.

17. A filtration unit in accordance with claim 16, wherein the metallic agent is in the form of a mesh and is silver, zinc, titanium, copper, or iron oxide.

18. A filtration unit in accordance with claim 11, wherein the active stage additionally comprises an IR light source electric or magnetic field generator.

19. A filtration unit in accordance with claim 13, wherein the active stage additionally comprises and electric or magnetic field generator to separate airborne particles from contaminated air.

20. A filtration unit in accordance with claim 13, wherein the electric or magnetic field generator includes microfilaments, micro electrical plates or magnetic coils.

21. A filtration unit in accordance with claim 13, wherein the active ingredient is in the form of a particulate, a tablet, a tape, a mesh, a solid containing the active ingredient, or a fabric containing the active ingredient.

* * * * *